United States Patent [19]
Yewer, Jr.

[11] Patent Number: 5,600,853
[45] Date of Patent: Feb. 11, 1997

[54] ORTHOPEDIC GLOVE AND METHOD OF MAKING SAME

[76] Inventor: Edward H. Yewer, Jr., 6259 N. Hwy. 83, Hartland, Wis. 53029

[21] Appl. No.: 284,868

[22] Filed: Aug. 2, 1994

[51] Int. Cl.[6] .................................................. A41D 13/10
[52] U.S. Cl. ................................... 2/161.1; 2/161.6; 2/20
[58] Field of Search .................... 2/16, 20, 21, 161.1, 2/161.6, 161.7, 163, 161.2, 168, 158; 602/21, 22, 6, 7, 62, 64; 473/201, 205; 483/44, 47, 49

[56] References Cited

U.S. PATENT DOCUMENTS

| | | | |
|---|---|---|---|
| D. 320,872 | 10/1991 | McCrane | D29/22 |
| 675,695 | 6/1901 | Whitcomb | 2/20 |
| 950,633 | 3/1910 | Eastman | 2/20 |
| 1,314,053 | 8/1919 | Eissler | 2/20 |
| 1,797,057 | 3/1931 | Foulke | 602/21 |
| 2,178,019 | 10/1939 | Knuteson | 2/20 |
| 2,322,710 | 6/1943 | Eisendrath | 2/20 |
| 3,065,472 | 11/1962 | Linnell | 473/205 |
| 3,421,761 | 1/1969 | Grant | 602/22 |
| 4,047,251 | 9/1977 | Stockum | 2/163 |
| 4,051,553 | 10/1977 | Howard | 2/161 |
| 4,295,229 | 10/1981 | Clark et al. | 2/20 |
| 4,326,706 | 4/1982 | Guthrie et al. | 272/119 |
| 4,558,694 | 12/1985 | Barber | 602/21 |
| 4,599,920 | 7/1986 | Schmid | 81/489 |
| 4,624,016 | 11/1986 | Luevano | 2/161 |
| 4,681,012 | 7/1987 | Stelma et al. | 2/163 |
| 4,977,621 | 12/1990 | Richard | 2/20 |
| 5,069,454 | 12/1991 | Frost | 273/165 |
| 5,088,124 | 2/1992 | Dutchnik | 2/168 |
| 5,180,165 | 1/1993 | Frost | 273/165 |
| 5,214,799 | 6/1993 | Fabry | 2/20 |
| 5,367,711 | 11/1994 | Calagui | 2/161.6 |

*Primary Examiner*—Amy B. Vanatta
*Attorney, Agent, or Firm*—Quarles & Brady

[57] ABSTRACT

A hand glove has ridge contours on its interior surface which cradle the base portions of the proximal phalanges of the fingers. A dome may also be formed on the interior surface which fits into the metacarpal arch of the palm. The glove may be molded to fit the contours of a hand, thereby reducing sewing operations.

15 Claims, 6 Drawing Sheets

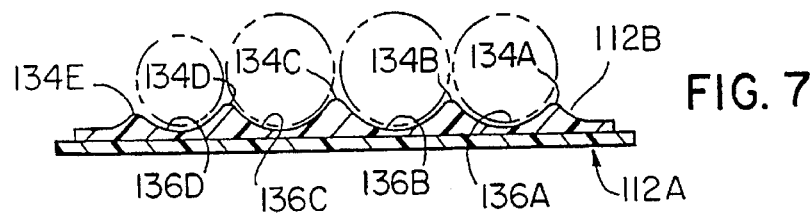
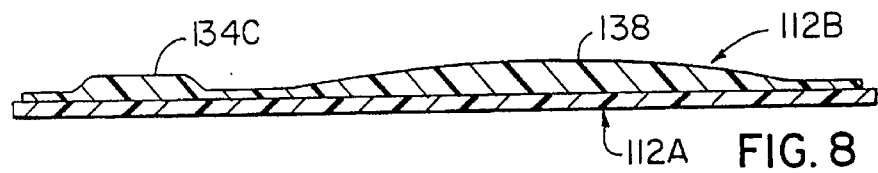
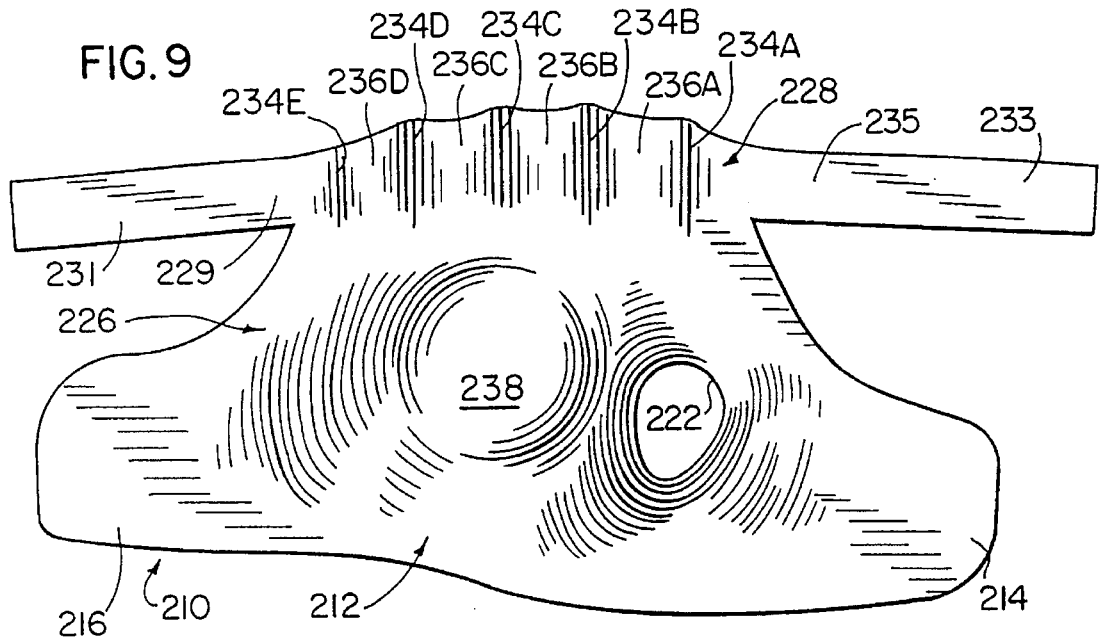
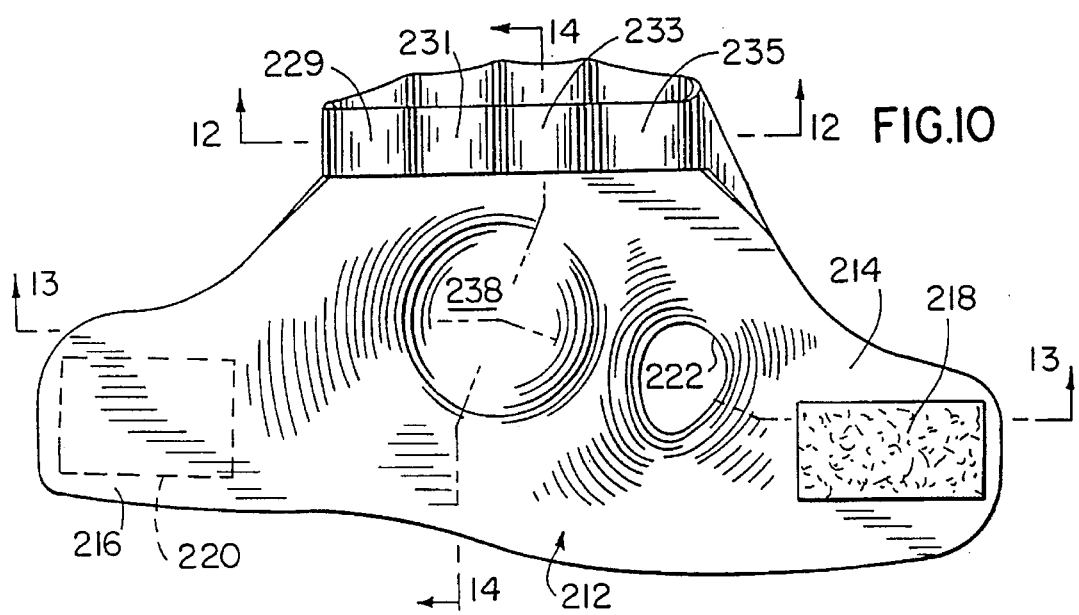

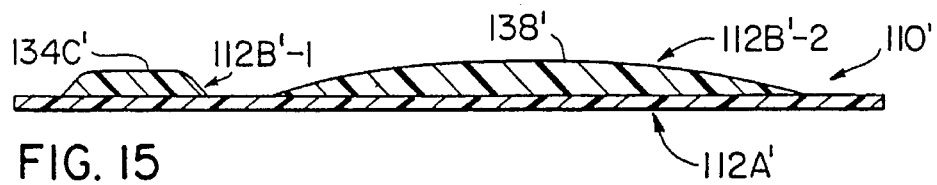
FIG. 15
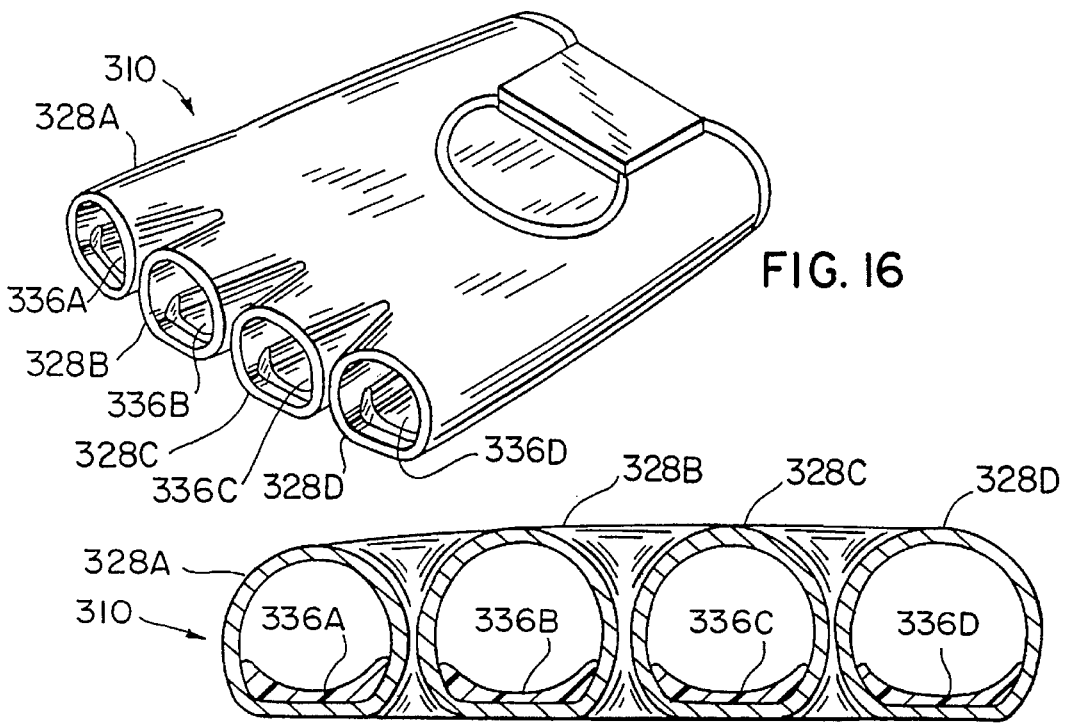
FIG. 16
FIG. 17
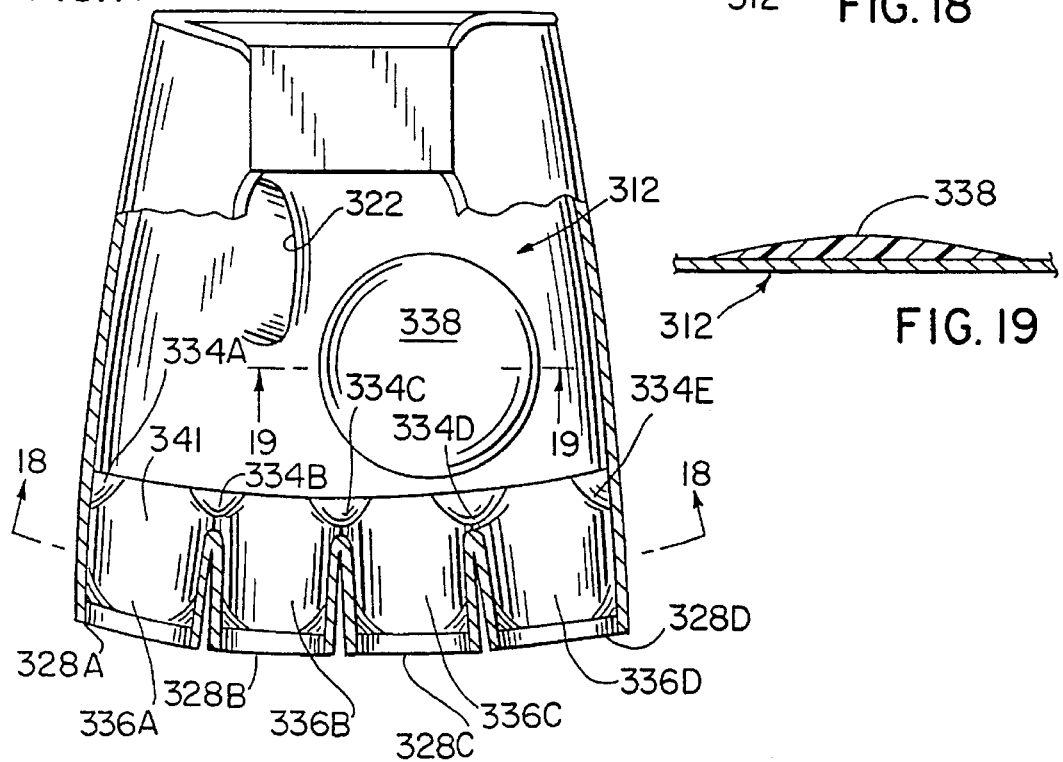
FIG. 18
FIG. 19

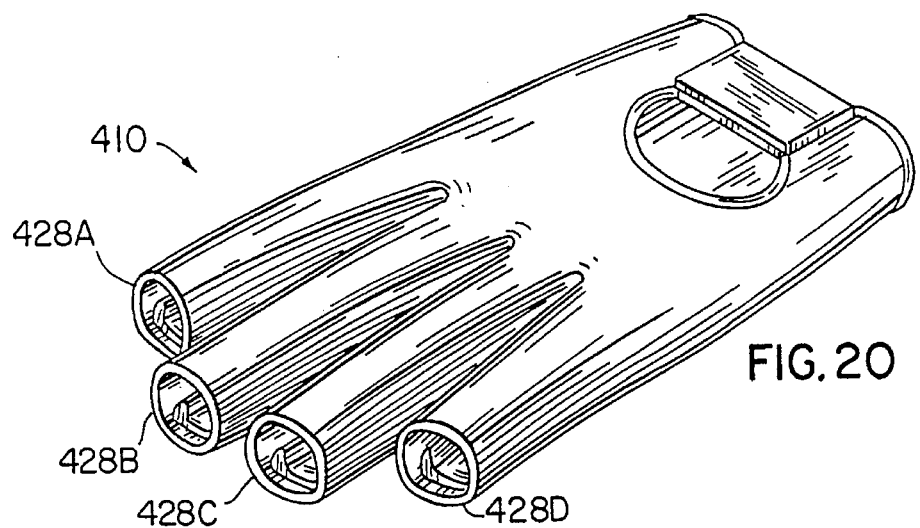
FIG. 20
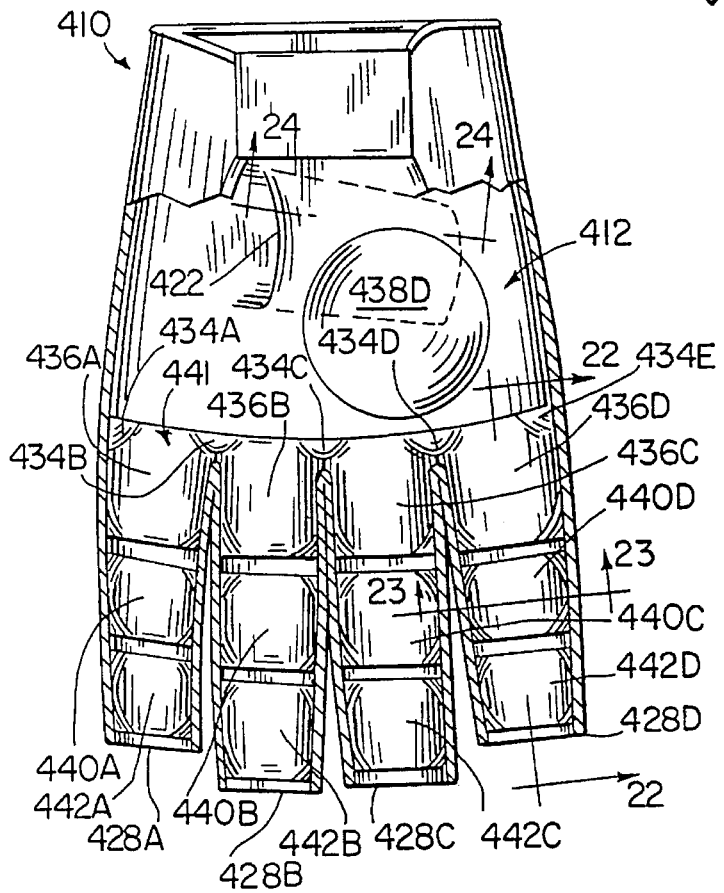
FIG. 21
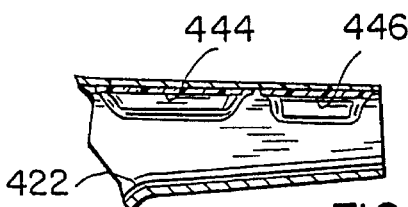
FIG. 24
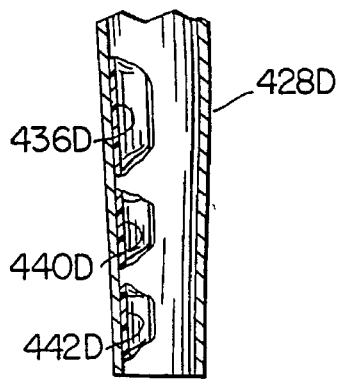
FIG. 23
FIG. 22

ORTHOPEDIC GLOVE AND METHOD OF MAKING SAME

BACKGROUND OF THE INVENTION

1. Field of the Invention

This invention relates to hand gloves, and particularly to a hand glove for enhancing the grip of a user and more uniformly transmitting load and/or vibration or shock to a hand in certain types of gripping activities.

In many types of home, industrial and sporting activities, it is necessary to grasp a cylindrical bar or ring, such as in weight lifting, bicycle riding, water skiing, motorcycle riding, driving a car or operating hand tools such as hammers, cutting tools, etc. While the human hand is well suited and adaptable to grasping many different shapes, repetitive grasping, particularly of these shapes, can result in repetitive motion injuries or strain and cumulative trauma disorders, such as carpal tunnel syndrome.

This is because the palmar surface of the hand, which is the surface of the hand which contacts the shape being grasped, is defined by the bones and soft tissue on the palmar side of the hand. These bones consist of five metacarpals which extend from the wrist up to the base of the fingers. The metacarpals have varying degrees of movement, with the thumb and little finger metacarpals having the most movement, and the index finger metacarpal having the least. These five metacarpals are dished, creating a metacarpal arch or concavity in the central portion of the palm.

At the distal ends of the metacarpals, the fingers are attached. The index, middle, ring and little fingers each have three phalanges, with the phalanx attached to the corresponding metacarpal being the proximal phalanx, the next phalanx being the middle, and the outer phalanx (at the fingertips) being the distal phalanx. The thumb has only two phalanges, a proximal and a distal.

When laying the hand palm down on a flat surface, most of the load is borne by the fingers and around the perimeter of the palm. Very little load is borne in the central part of the palm due to the metacarpal arch. In addition, when grasping a cylindrical bar, much of the load is borne by the palmar surface along a line which extends across the bases of the proximal phalanges of the index, middle, ring and little fingers. Grasping such an object also loads the base of the proximal phalanx of the thumb. These loads at the base portions of the fingers are most concentrated at the immediate inside, or 0° position (See FIG. 3 the little, ring, middle and index finger), of the fingers and is only spread to the sides of the base portions of the fingers by whatever stable soft tissue the user has in that area. Also, such loading can tend to rotate the fingers with undesirable effects.

The present invention seeks to enhance hand gripping, particularly of a straight (like a handle bar) or curved (like a steering wheel) cylindrical shape to help reduce hand strain and injuries and increase stamina.

SUMMARY OF THE INVENTION

The invention provides a hand glove which spreads gripping loads over a larger area of the hand, stabilizes and increases gripping power, reduces fatigue, finger rotation and adds to comfort when gripping certain shapes. The glove has a palm panel for extending over the palm of a hand and over a base portion of the proximal phalanx of at least one finger. The palm panel has an exterior surface facing away from the hand and an interior surface facing the hand. The interior surface defines at least two ridges, one of the ridges extending on each side of the base portion. The ridges define between them a cradle for the base portion of the proximal phalanx. Thereby, especially when gripping a straight or curved cylindrical object, the cradle spreads the gripping load from the exterior surface to an arc around the inner side of the base of the finger, which improves stability, strength and comfort.

Preferably, the palm panel extends over the base portions of multiple proximal phalanges of the hand and the interior surface defines ridges along both sides of multiple base portions which cradle the base portions, so as to spread the gripping load over more fingers.

In another useful aspect, the palm panel is thicker in a central area of the palm and tapers outwardly to generally fit into a metacarpal arch of the palm on the interior side of the palm panel. In this aspect, the shape of the palm panel in the central area of the palm may be defined by one piece of material and the shape of the ridges defined by at least one other piece of material which is separate from the one piece of material. Thereby, wrinkling or bunching up of the glove between the ridges and the central area can be avoided, because the material in that area can be the pliable material of the glove body.

In this respect, the shape of the interior and exterior surfaces of the palm panel may be defined by a unitary piece of material, or may be defined by at least two separate pieces of material which are connected together. For example, a glove body may define the shape of the exterior surface of the palm panel and a molded insert attached to the glove body may define the shape of the interior surface. Further, one molded insert may define the shape of the central portion and a separate molded insert may define the shape of the ridges.

In one embodiment, the palm panel includes a central portion covering the palm and at least one finger portion extending from the central portion over a base portion of a proximal phalanx, the ridges being provided on an interior surface of the finger portion. In this aspect, the palm panel may include multiple finger portions, a pair of ridges defining a cradle between them being defined on the interior surface of each of multiple finger portions, and the finger portions being separated from one another. Thus, the invention may be incorporated into gloves having separate finger portions or in gloves in which a continuous panel extends across the fingers, and may be applied to cover some or all of the phalanges of the fingers, including the thumb.

In another aspect of the invention, a glove is made of a moldable sheet material so that it can be formed, for example with the application of heat and pressure, to more closely conform to the shape of a human hand, and thereby eliminate sewing operations otherwise necessary to put darts into the fabric so as to make it fit a hand.

BRIEF DESCRIPTION OF THE DRAWINGS

FIG. 7 is a sectional view as viewed from the plane of the line 7—7 of FIG. 6;

FIG. 8 is a sectional view as viewed from the plane of the line 8—8 of FIG. 6;

FIG. 9 is an interior side plan view of a third embodiment of the invention shown before finger loops are stitched to the palm portion of the glove;

FIG. 10 is a view similar to FIG. 9 but shown with the finger loops stitched to the palm portion;

FIG. 15 is a view similar to FIG. 8 but showing a fourth embodiment of the invention;

FIG. 16 is a perspective view of a fifth embodiment of a glove of the invention which has separate and circumferentially closed fingers;

FIG. 17 is a top plan view of the glove of FIG. 16 shown with a portion broken away;

FIG. 18 is a sectional view as viewed from the plane of the line 18—18 of FIG. 17;

FIG. 19 is a sectional view from the plane of the line 19—19 of FIG. 17;

FIG. 20 is a perspective view of a sixth embodiment of a glove of the invention which has separate circumferentially closed and longer fingers;

FIG. 21 is a top plan view of the glove of FIG. 20 shown with a portion broken away;

FIG. 22 is a sectional view as viewed from the plane of the line 22—22 of FIG. 21;

FIG. 23 is a sectional view from the plane of the line 23—23 of FIG. 21; and

FIG. 24 is a sectional view from the plane of the line 24—24 of FIG. 21.

DETAILED DESCRIPTION OF THE PREFERRED EMBODIMENTS

Figure 1:
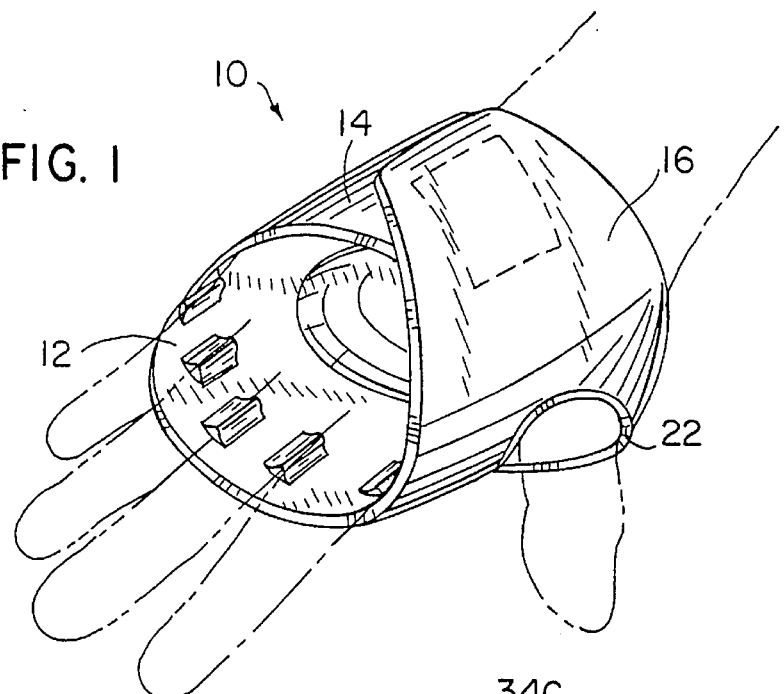
FIG. 1 is a perspective view of a sports glove of the invention, shown wrapped around a hand which is shown in phantom.
Figure 2:
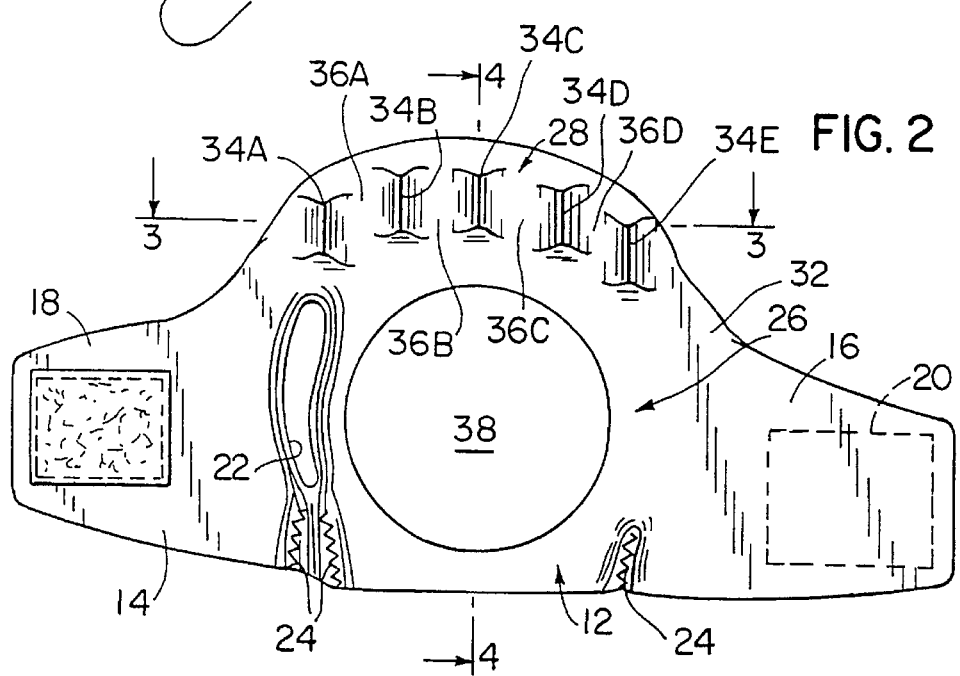
FIG. 2 is an interior side plan view of the glove of FIG. 1.
Figure 3:
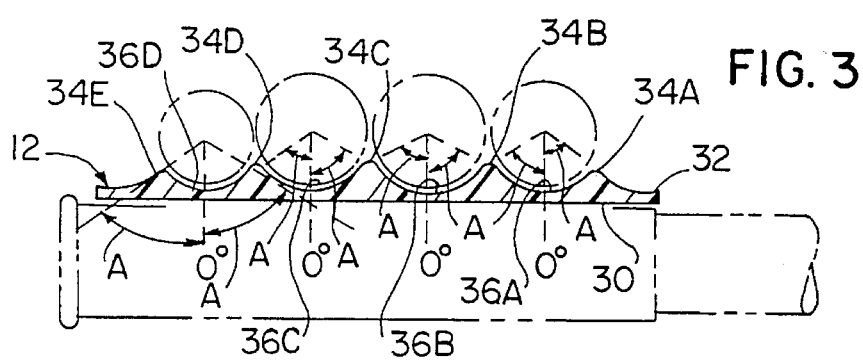
FIG. 3 is a sectional view as viewed from the plane of the line 3—3 of FIG. 2 and with a straight cylindrical bar being grasped shown in phantom and the index, middle, ring and little fingers shown in phantom.
Figure 4:
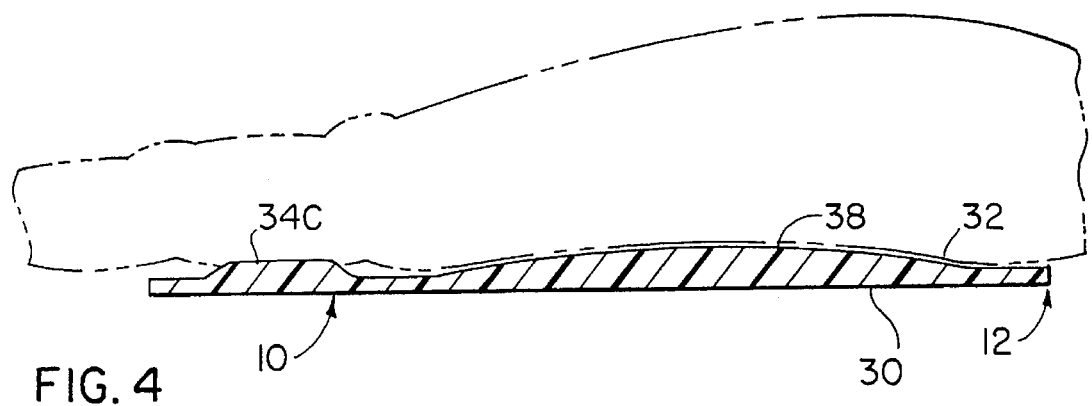
FIG. 4 is a sectional view of the glove as viewed from the plane of the line 4—4 of FIG. 2 and illustrates a hand in phantom.
Figure 5:
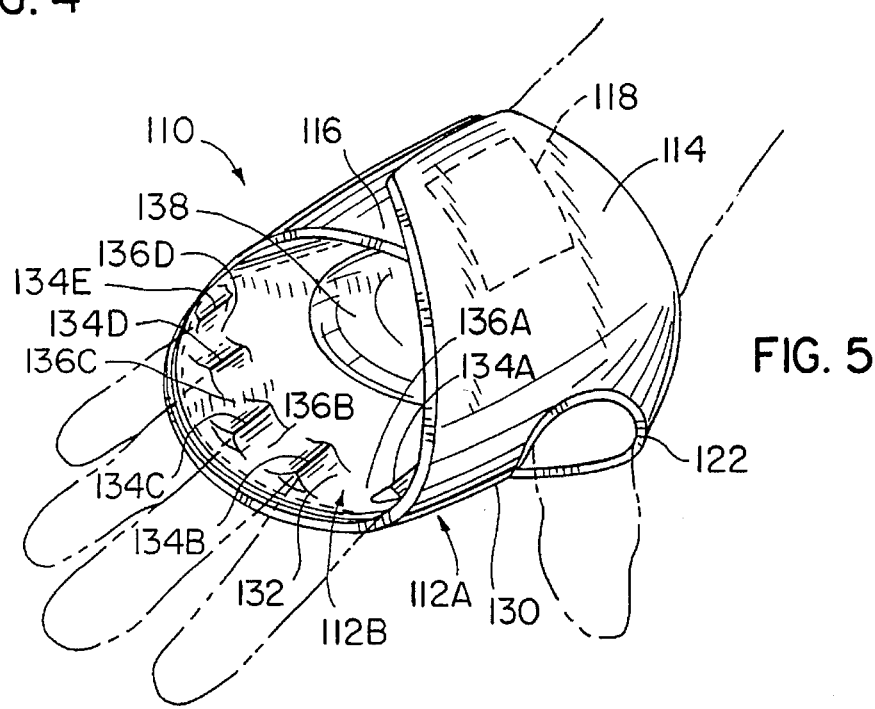
FIG. 5 is a view similar to FIG. 1 but illustrating a second embodiment of a glove of the invention.
Figure 6:
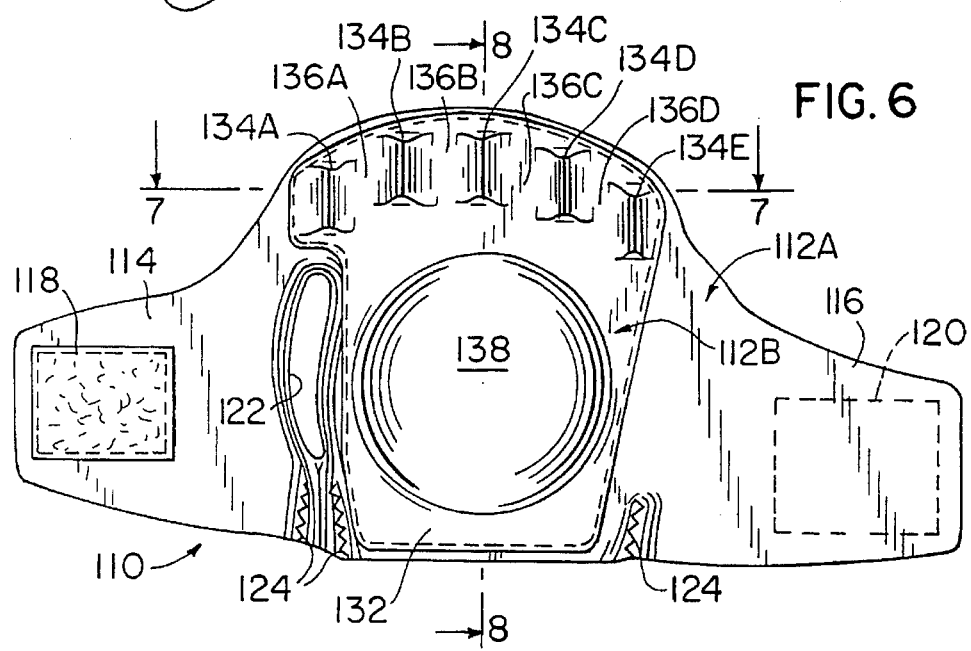
FIG. 6 is a view similar to FIG. 2 but of the second embodiment.
Figure 11:
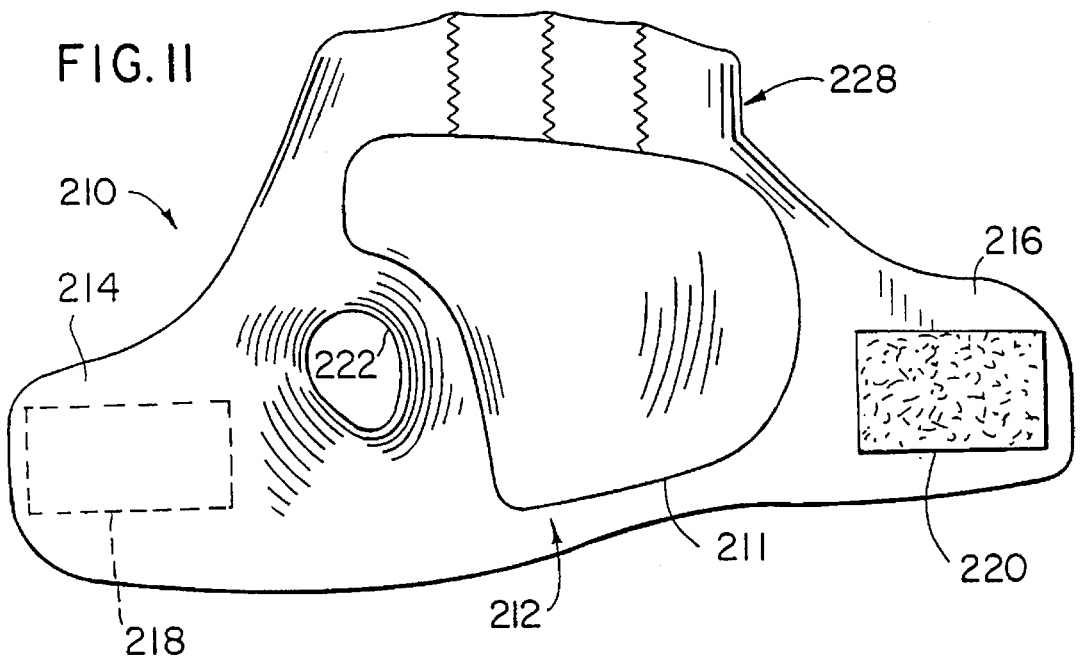
FIG. 11 is an exterior side plan view of the glove of FIGS. 9 and 10.

FIGS. 1–4 illustrate a first embodiment 10 of the invention. The glove 10 includes a palm panel 12 and first 14 and second 16 closure tabs integrally joined with the palm panel 12. A hook and loop type fastener patch is stitched on the exterior surface of the first closure tab 14 and a mating hook and loop type patch 20 is stitched on the tab 16 so as to enable securing the first tab 14 to the second tab 16 so as to close the glove 10 around the user's hand as shown in FIG. 1. A thumb hole 22 is formed in the glove 10 between the palm panel 12 and tab 14 and darts 24 are sewn into the wrist edge of the glove 10 to make the glove 10 conform more closely to the shape of a human hand.

The palm panel 12 has a central portion 26 which overlies the palm of a user's hand and has a finger portion 28 which extends over the base portions of the proximal phalanges of a user's index, middle, ring and little fingers. The exterior surface 30 of the palm panel 12 is generally flat (when unstressed). The interior surface 32 is shaped to define formations in accordance with the invention.

Specifically, ridges 34A–E are formed on the interior surface 32 which extend longitudinally along and between the base portions of the proximal phalanges of the user's fingers. Each pair of adjacent ridges 34A–E forms a cradle 36A–D between them which generally fits the base portion of the user's finger which is received by the respective cradle. Thereby, loads borne along the finger portion 28 are not only borne at the 0° position of each finger (shown in FIG. 3) but are transmitted to the finger for a substantial arc A on each side of the 0° position. The ridges 34A–E and cradles 36A–D also help support the muscle and soft tissue at the base portion of the fingers to prevent it from being excessively squashed or pinched between the finger bones and the rod or other object being grasped.

In addition, the interior surface 32 of the central portion 26 is domed so as to be increased in thickness at the central portion of the user's palm and taper outwardly therefrom so as to generally fit into the metacarpal arch of the palm and provide a generally flat surface on the exterior surface 30 so as to help transmit loads uniformly from the exterior surface 30 to the user's palm area.

The glove 10 can be made of any suitable material which is pliable and can be formed to have the ridges 34A–E and the dome 38. This can be accomplished with many different types of foam, rubber or neoprene, silicone, elastomer or shape retaining gel materials, and these materials may or may not be laminated with cloth. For example, one type of material which could be used is a fabric covered neoprene which is typically approximately 3 millimeters in thickness, although the thickness may vary when the material is heat and/or compression molded to have the ridges 34A–E and the dome 38. If vibration isolation of the hand is desired, then a gel material may be preferred.

The ridges 34A–E and dome 38 can be formed by pressing the material between two heated dies, one of which is flat to define the exterior surface and the other of which is the negative shape of the interior surface 32.

Materials which can be hot molded in this manner are well known. One such material is fabric covered neoprene, as stated above, and another is fabric covered polyethylene foam, which is also desirable for its elastic properties and also because it provides cushioning. The fabric covering for such foam or neoprene may be any suitable fabric, preferably also elastic, such as nylon or Lycra™. Terry cloth may also be used. Foam suitable for making the glove 10 is available from Voltec Division of Sekisui American Corporation of Lawrence, Mass.. It is preferably a four pound "A" grade 100% polyethylene foam known as "Volara", which is approximately ¼ inch thick prior to heat/compression molding. This material is radiation cross linked, as opposed to chemical cross linking. The material used may be provided with small holes (for example, holes randomly distributed over a total of 10°–20° of the area) for venting. However, the invention is not limited to any particular type of foam, to foams in general, or to any other particular material, but is applicable to any material which can be formed to provide the ridges 34A–E.

FIGS. 5–8 disclose a second embodiment 110 of the invention which is nearly identical to the glove 10 except that the palm panel 112 is made in two pieces, with a glove body 112A providing the exterior surface 130 and an insert 112B sewn on the interior surface of the body 112A providing the interior surface 132 which defines the ridges 134A–E and dome 138. In the embodiment 100, the same reference numerals are used to describe elements corresponding to elements of the glove 10, plus 100. The insert 112B is sewn to the body 112A as indicated by the dashed lines around the perimeter of the insert 112B in FIG. 6. In this embodiment, the insert 112B may be made by a casting or injection molding process, of foam, rubber, neoprene, gel or other suitable flexible shape retaining material.

A variation on the embodiment 110 is shown in FIG. 15. This variation is identified by the same reference numerals as the embodiment 110, but with a prime (') sign. The only difference between the glove 110' and the glove 110, is that the insert 112B is made in two pieces, with one portion 112B'-1 of the insert providing the ridges 134A–E and another portion 112B'-2 providing the dome 138'.

Still another embodiment is shown in FIGS. 9–14. Elements in this embodiment corresponding to elements of the glove 10 are identified by the same reference numerals, plus 200.

The glove 210 is essentially the same as the glove 10, except that instead of having darts 24 to make the glove conform to the shape around a user's wrist, the glove 210 is hot formed into that shape. This is accomplished by pressing a sheet of heat formable material such as neoprene or polyethylene foam against a hot die which is in the shape of a human hand and cooling the material until it sets in the desired shape, thereby eliminating the sewing necessary to make the darts 24, while still providing a good fit. It is also noted that in the forming operation, the material around the thumbhole 224 can be extruded out to more closely fit around and extend up over the base portion of the thumb.

Figure 12:
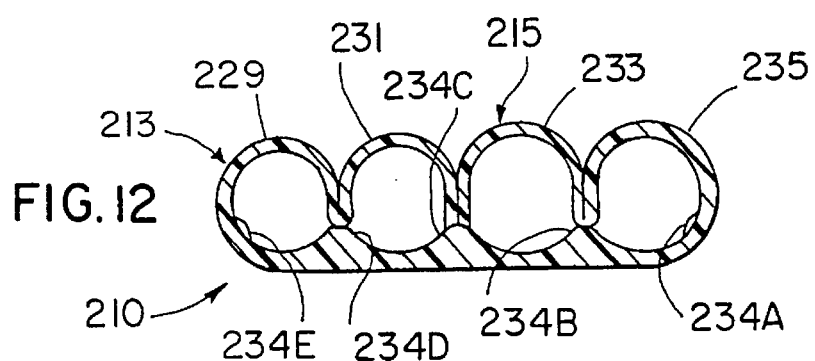
FIG. 12 is a sectional view as viewed from the plane of the line 12—12 of FIG. 10.
Figure 13:
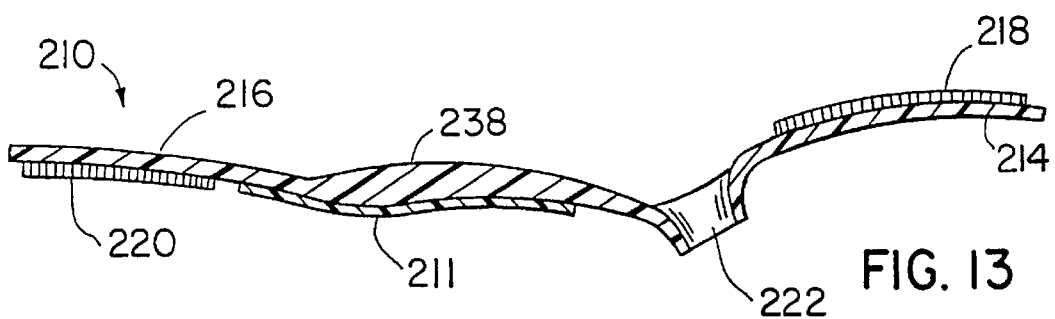
FIG. 13 is a sectional view as viewed from the plane of the line 13—13 of FIG. 10.
Figure 14:
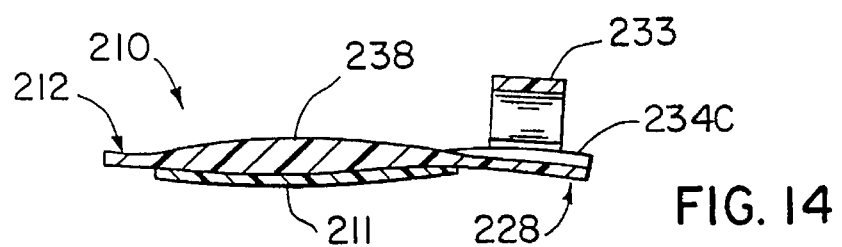
FIG. 14 is a sectional view as viewed from the plane of the line 14—14 of FIG. 10.

In addition, the glove 210 is provided with a grip pad 211 on the exterior surface of the palm panel, which may be a piece of neoprene which is not fabric covered, and also has straps 213 and 215 which are sewn to the finger portion 228 to create finger loops. It should be understood that a glove of the invention could be provided with or without the grip pad and with or without finger loops 229, 231, 233 and 235. As shown in FIG. 12, the glove 210 has ridges 234A–E. In addition, as shown in FIGS. 13 and 14, the glove 210 has a thickened dome area 238 in a central portion of the palm panel 12.

Another embodiment 310 of the invention is shown in FIGS. 16–19. Elements corresponding to the elements of the glove 10 are identified by the same reference number, plus 300.

As illustrated by the embodiment 310, ridges 334A–E can be provided in gloves of the type which have a palm panel with separate finger portions 328A–D. In this respect, a pair of ridges which provides a cradle 336A–D between them is provided in each finger portion. This may be done either with an insert, or by molding the ridges directly into the palm panel. If done with an insert, the ridges could be provided by separate inserts, or by a single insert with the individual finger portions of the insert emanating from a common base portion 341 (FIG. 17) and the ridges 334A–E are split down the middle so that they can extend into the finger portions.

One advantage of providing the ridges and/or dome with separate inserts is that thereby the invention can be incorporated with glove bodies made of materials which are not moldable, such as leather, cotton, or other fabric materials.

FIGS. 20–24 illustrate still another embodiment 410. Elements corresponding to the elements of the glove 10 are identified by the same reference number, plus 400. The main difference between the glove 410 and the previously described gloves is that the glove 410 has full fingers, including for the thumb, except for being open at the finger tips. A cradle 436A–D is provided for each proximal phalanx of the little, ring, middle and index fingers. In addition, cradles 440A–D are provided for the middle phalanges and cradles 442A–D are provided for the distal phalanges. Furthermore, a cradle 444 is provided for the proximal phalanx of the thumb (FIG. 24) and a cradle 446 is provided for the distal phalanx of the thumb. All of these cradles are defined between ridges and are positioned to wrap around the palmar sides of the fingers. In the glove 410, the cradles may be held in place by stitching, bonding with a glue or adhesive or any other suitable means. Preferably the cradles are separated at the distal and middle joints of the little, ring, middle and index fingers, and at the distal joint of the thumb to allow for flexibility without bunching up of material when those joints are flexed.

The invention thereby provides an orthopedic glove which helps uniformly distribute loads to the hand and contributes to stability and strength in gripping an object, particularly such objects which have straight surfaces across the fingers and/or palm area of the hand. For example, a cylindrical rod is straight in the longitudinal direction and when gripped by a user typically the longitudinal direction extends across the base of the fingers, making a glove of the present invention well suited to gripping this shape. In addition cylindrical rods which are curved with a relatively large radius, such as an automotive or boat steering wheel, are also suited for being gripped by a glove of the invention.

Preferred embodiments of the invention have been described in considerable detail. Many modifications and variations to the invention will be apparent to those of ordinary skill in the art. For example, the invention could be applied to a glove having closed finger tips, for example by enclosing the finger tips of the glove 410. Gloves of the invention could also be made using a casting or dipping process, in which a hand shaped form or fabric liner is dipped in a latex or rubber which when cured provides the exterior surface of the glove. Pads defining the dome shape of the palm panel and the finger ridges could be incorporated into the hand form or into the fabric liner prior to dipping, to define the shape of the interior surface of the glove after dipping. Such dipping processes are well known and commercially practiced, for example by Guardian Manufacturing Company of Willard Ohio, Ansell Edmont Industrial of Coshocton, Ohio and others. In such a glove, the contours provided by the invention would help reduce the strength and energy required to hold an object, and especially if rubber or gel padding material were used, would reduce vibration transmitted to the hand.

Therefore, the invention should not be limited to the embodiments described, but should be defined by the claims which follow.

I claim:

1. A hand glove, comprising:

a pliable palm panel for extending over the palm of a hand and over a base portion of the proximal phalanx of at least one finger, said palm panel having an exterior surface facing away from the hand and an interior surface facing the hand;

wherein on said interior surface there is defined at least two pliable ridges by thickenings of said palm panel, one of said ridges extending on each side of said base portion, said ridges defining between them a cradle for said base portion of said proximal phalanx.

2. A hand glove as claimed in claim 1, wherein thickenings of said palm panel define on said interior surface ridges on both sides of at least two fingers.

3. A hand glove as claimed in claim 1, wherein said thickenings define ridges on said interior surface on both sides of four fingers.

4. A hand glove as claimed in claim 1, wherein said palm panel extends over the base portions of multiple proximal phalanges of the hand and said thickenings define ridges on said interior surface along both sides of multiple base portions which cradle said base portions.

5. A hand glove as claimed in claim 1, wherein said palm panel is thicker in a central area of the palm and tapers outwardly to generally fit inside a metacarpal arch of the palm on the interior side of said palm panel.

6. A hand glove as claimed in claim 5, wherein the shape of said palm panel in the central area of the palm is defined by one piece of material and the shape of said ridges is defined by at least one other piece of material which is separate from said one piece of material.

7. A hand glove as claimed in claim 1, wherein the shape of said interior and exterior surfaces of said palm panel are defined by a unitary piece of material.

8. A hand glove as claimed in claim 1, wherein the shape of said interior and exterior surfaces of said palm panel are defined by at least two separate pieces of material which are connected together.

9. A hand glove as claimed in claim 8, wherein a glove body defines the shape of said exterior surface of said palm panel and a molded insert attached to said glove body defines the shape of said interior surface.

10. A hand glove as claimed in claim 9, wherein at least two molded inserts define the shape of said interior surface, one of said inserts defining said ridges and another of said inserts defining a thickened central area of said palm panel which tapers outwardly to generally fit inside a metacarpal arch of the palm on the interior side of said palm panel.

11. A hand glove as claimed in claim 1, wherein said palm panel includes a central portion covering said palm and at least one finger portion extending from said central portion over a base portion of a proximal phalanx, said ridges being provided on an interior surface of said finger portion.

12. A hand glove as claimed in claim 1, wherein said palm panel includes a central portion covering said palm and at least one finger portion extending from said central portion over proximal, middle and distal phalanges of a finger, said ridges being provided on an interior surface of said finger portion to define cradles between said ridges over said proximal, middle and distal phalanges.

13. A hand glove as claimed in claim 1, wherein said palm panel includes a central portion covering said palm and at least one thumb portion extending from said central portion over proximal and distal phalanges of a thumb, said ridges being provided on an interior surface of said thumb portion to define cradles between said ridges over said proximal and distal phalanges.

14. A hand glove as claimed in claim 11, wherein said palm panel includes multiple finger portions, a pair of ridges defining a cradle between them being defined on the interior surface of each of multiple finger portions, and said finger portions are separated from one another.

15. A hand glove, comprising:

a palm panel for extending over the palm of a hand and at least one back panel for extending over the back of the hand, said palm panel and said back panel being made of pliable sheet material which is formed into the exterior shape of a human hand, said palm panel varying in thickness to define contours of a human hand including on an interior surface of said palm panel finger cradles defined by ridges alongside said fingers and a dome which fits inside said metacarpal arch.

* * * * *